United States Patent [19]

Salvestro et al.

[11] Patent Number: 5,020,933
[45] Date of Patent: Jun. 4, 1991

[54] LOCKING MECHANISM FOR MEDICAL DEVICES

[75] Inventors: Aldo T. Salvestro; Rainer M. Bohl, both of Vancouver, Canada; Martin L. Furse, Dallas, Tex.

[73] Assignee: Andronic Devices, Ltd., British Columbia, Canada

[21] Appl. No.: 401,838

[22] Filed: Sep. 1, 1989

[51] Int. Cl.$^5$ ............................................. F16C 11/06
[52] U.S. Cl. ........................................ 403/90; 403/55; 403/24
[58] Field of Search ................ 403/90, 55, 56, 114, 403/115, 24

[56] References Cited

U.S. PATENT DOCUMENTS

| 2,672,313 | 3/1954 | Poole | 403/90 X |
| 3,638,973 | 2/1972 | Poletti | 403/90 X |
| 3,675,953 | 7/1972 | Glatz | 403/90 |
| 4,807,618 | 2/1989 | Auchinleck et al. | 128/878 |

FOREIGN PATENT DOCUMENTS

| 547982 | 10/1957 | Canada | 403/90 |
| 1317518 | 1/1963 | France | 403/90 |
| 619702 | 8/1978 | U.S.S.R. | 403/90 |

Primary Examiner—Andrew V. Kundrat
Attorney, Agent, or Firm—Klarquist, Sparkman, Campbell, Leigh and Whinston

[57] ABSTRACT

Apparatus useful in surgery for holding retractors and other surgical instrumentation in a number of different positions required by a surgeon for the performance of a surgical procedure, including advanced sensing and regulation of retraction pressures and position; and incorporating a force amplification method to drive a locking mechanism in the supporting structure that utilizes a constrained, substantially incompressible, flexible solid material to yield a mechanism that is suitable for clinical use.

8 Claims, 4 Drawing Sheets

LOCKING MECHANISM FOR MEDICAL DEVICES

FIELD OF THE INVENTION

This invention pertains to a sterilizable apparatus for positioning retractor blades in a number of different orientations required by a surgeon for the performance of a surgical procedure, and to a means for automatically adjusting the position of a retractor blade in response to sensed physiological or morphological parameters. In particular, this invention pertains to apparatus comprising a plurality of positioning members interconnecting a means for holding retractor blades to a supporting point, each member including selectably positionable joints which may be locked in a selected position. The invention further comprises a force multiplication method which utilizes a constrained, substantially incompressible, flexible material to yield a sterilizable and clean force multiplier. The invention also includes means for sensing the pressure in tissue near a location under a retractor blade, means for measuring the position of the retractor blade with respect to a fixed point, and means for changing the position of the retractor blade, so that the position of the retractor blade can be automatically adjusted to apply a controlled pressure or displacement to tissue.

BACKGROUND OF THE INVENTION

Many surgical procedures require that surgical instruments such as retractor blades be positioned in a number of different positions in order to perform a certain surgical task. It is desirable that the operating surgeon or surgical assistant be able to directly move the retractor blade into various positions and configurations that may be required. It is also desirable that any surgical retractor that may be used to achieve such positions and configurations not obstruct the surgical site, and be able to avoid any obstacles that may exist around the surgical site, such as medical imaging systems, operating room lights, instrument trays, or other apparatus. The surgical retractor should also be stable, easy to control and re-position precisely, require no attention between changes in position in order to free the surgeon's hands to perform other tasks, and be sufficiently strong and rigid to hold a set position reliably, yet be light enough to allow the surgeon to easily achieve a desired position and orientation of the retractor blade. It is also desirable that the surgical retractor sense pressures in the retracted tissue near a location under the retractor blade, alert the surgeon of any potentially hazardous pressures, and automatically regulate retraction pressures and positions, thereby reducing the likelihood of tissue laceration and ischemia caused by the retractor blade during long procedures.

Various methods for positioning and holding retractor blades are known in the prior art. One common method for positioning a retractor blade is to have a surgical assistant hold the retractor blade in a desired position, and change the position when and as requested by the operating surgeon. This task is fatiguing for the surgical assistant, and may not provide sufficiently precise and rigid support for the retractor blade in some surgical procedures.

In addition to the method for positioning described above, apparatus for positioning retractor blades exists in the art. One typical retractor blade positioning apparatus consists of a vertical mounting frame fastened to the operating room table, to which are fastened at discrete but adjustable positions different retractor blades to provide an upward pulling force on tissues or organs (e.g. Aesculap BT710 Fixation Device and Aesculap BT711-BT715 Rochard abdominal retractor blades, Aescualp Instruments Corp, Burlingame, Calif., U.S.A.). Ropes, weights, and pulley systems are also used in conjunction with the vertical frame to provide a continuously adjustable positioning system. Similar abdominal retraction techniques utilize a horizontal frame laid on the patient's body to which are fastened at discrete but adjustable positions different retractor blades to provide a lateral pulling force on tissues or organs (e.g. Aesculap BV662 frame and Aesculap BV668 blades). These types of surgical retractors are difficult to set up and take down, clumsy to adjust, and often obstruct the surgical site. Furthermore, adjusting such apparatus to achieve a new position may require the assistance of a non-sterile person, in that operating room fixtures and support stands that may require re-positioning are not considered sterile, hence cannot be touched by a surgeon. This may preclude optimal positioning of the retractor blades or tissue, as the surgeon may no longer have direct control over the final position of the retractor blade. These types of retractor blade positioning systems are limited in their range of adjustment, versatility of orientation, precision of positioning, and rigidity of support. They also offer no means to sense and regulate applied retraction pressures.

Additional specialized positioning devices for holding retractor blades are known in the art. The Elmed Company of Addison Illinois manufactures a multi-jointed mechanism, the "Elmed Retract-Robot", catalog number 15088-00 single arm instrument, which can be locked in a wide range of positions with a thumb-screw arrangement. However this device is not suitable for a wide range of surgical procedures due to its inconsistent locking strength, limited range of motion, inability to unlock joints separately for re-positioning, time-consuming and tedious adjustment of the thumb screw, potential for obstruction of the surgical site, and solid steel construction which is not x-ray translucent. It is conceivable that several such devices could be connected together to create a larger structure with an increased range of motion, but such a structure would be very difficult to re-position, in that each device in the structure would have to be unlocked, positioned and locked individually each time a new position is required. In addition, it is unlikely that several such devices connected together would offer sufficient strength for the intended application. Finally, this device offers no means for sensing or regulating retraction pressures.

Also known in the art is a retractor blade holding device, widely known by surgeons throughout the world as a "Greenberg" brain retractor. This surgical retractor consists of a plurality of ball and socket joints, threaded upon a length of cable. This cable may be tightened with a lever mechanism to increase the friction between each ball and socket joint. The Greenberg brain retractor is not suitable for all surgical procedures due to its typically small size. In addition, the strength of the ball and socket joints when fully locked is insufficient to support the loads typically expected when positioning retractor blades in many surgical procedures. The device is not x-ray translucent, nor is it capable of sensing or regulating retraction pressure.

One problem that is common to any re-positionable surgical retractor is achieving sufficient strength and rigidity to provide a stable structure for the intended application, using only materials and mechanisms that are sterilizable, self-contained, and suitably clean for use in surgical procedures. Although many examples of locking mechanisms are known in the prior art, most are either too large, too weak when scaled down to a size appropriate for this application, or use fluid in a force multiplying system which is unsuitable in surgical applications due to concerns about leaks. In addition, the use of fluid as a force multiplying component requires that some means be provided to bleed air or other gasses from the fluid to render it substantially incompressible, which requires complex and specialized apparatus. A better means of achieving force multiplication would use a material which provides the function of a hydraulic amplifier over a very small range of motion, but which does not use fluids.

One example of a locking mechanism suitable for use in a non-sterile surgical environment is disclosed in U.S. Pat. No. 4,807,618, entitled "Patient Limb Positioning Apparatus". This apparatus uses a pneumatic actuator which exerts a high force on a system of levers which in turn exert force on a ball joint mechanism in order to lock it in place. This force multiplying mechanism is not suitable for use in applications where the device must be sterilized, because the materials and mechanisms used will not withstand the sterilization procedures used in hospitals. A further disadvantage of this type of mechanism is that it requires a relatively large number of very high strength components in order to operate properly.

SUMMARY OF THE INVENTION

The present invention provides apparatus for holding a retractor blade in a number of different positions required by a surgeon for the performance of a surgical procedure, while sensing the pressure in the retracted tissue near a location beneath the retractor blade, adjusting the position of the retractor blade in order to regulate the pressure in the retracted tissue, and indicating to the surgeon any excessive pressures applied to the retracted tissue. A surgical retractor in accordance with the invention consists of a sensing means for sensing tissue retraction pressure, a grasping means for holding retractor blades, an activating means for changing the position of the retractor, a sensing means for sensing the position of the retractor, a control means for controlling the position of the retractor blade in response to the sensed pressure and sensed position. The surgical retractor further comprises one or more positioning members interconnecting a supporting point to the grasping means, each positioning member having selectably positionable joints attached to attaching means for connecting each positioning member to other such members, or to the grasping means or to the supporting point. Each positioning member also includes a locking means for locking the selectably positionable joints in a selected position, an actuating means for locking and unlocking the locking means in response to a control signal, and a control signal generating means by which an operator can generate control signals for locking and unlocking either individual joints, or predefined groups of joints simultaneously.

In another aspect, the invention provides a force amplification method to drive a locking mechanism, that utilizes a constrained, substantially incompressible, flexible solid material to yield a force multiplier that is sterilizable and suitably sealed, self-contained, and clean for use in surgical procedures.

Another object of the invention is to improve the performance of a force multiplier by using a flexible solid material that is made of non-homogeneous material, and wherein the non-homogeneous material may be selected to have regions of varying hardness so as to increase the reliability of the force multiplier.

Another object of the invention is to provide a surgical retractor consisting of a plurality of positioning members, in which said positioning members may be individually re-positioned without having an effect upon the rest of the members making up the apparatus.

Other objects of the present invention include: providing a mechanism for attaching and detaching a wide variety of retractor blades to the surgical retractor, providing a control signal generating means for locking and unlocking the surgical retractor which is attached to the surgical retractor such that an operator must be in contact with the surgical retractor to unlock it, and providing a surgical retractor that may be largely constructed out of X-ray translucent materials so that the positioning members will minimally interfere with medical X-ray images taken of the body while a surgical retractor is being used.

DETAILED DESCRIPTION OF THE PREFERRED EMBODIMENT

Figure 1:
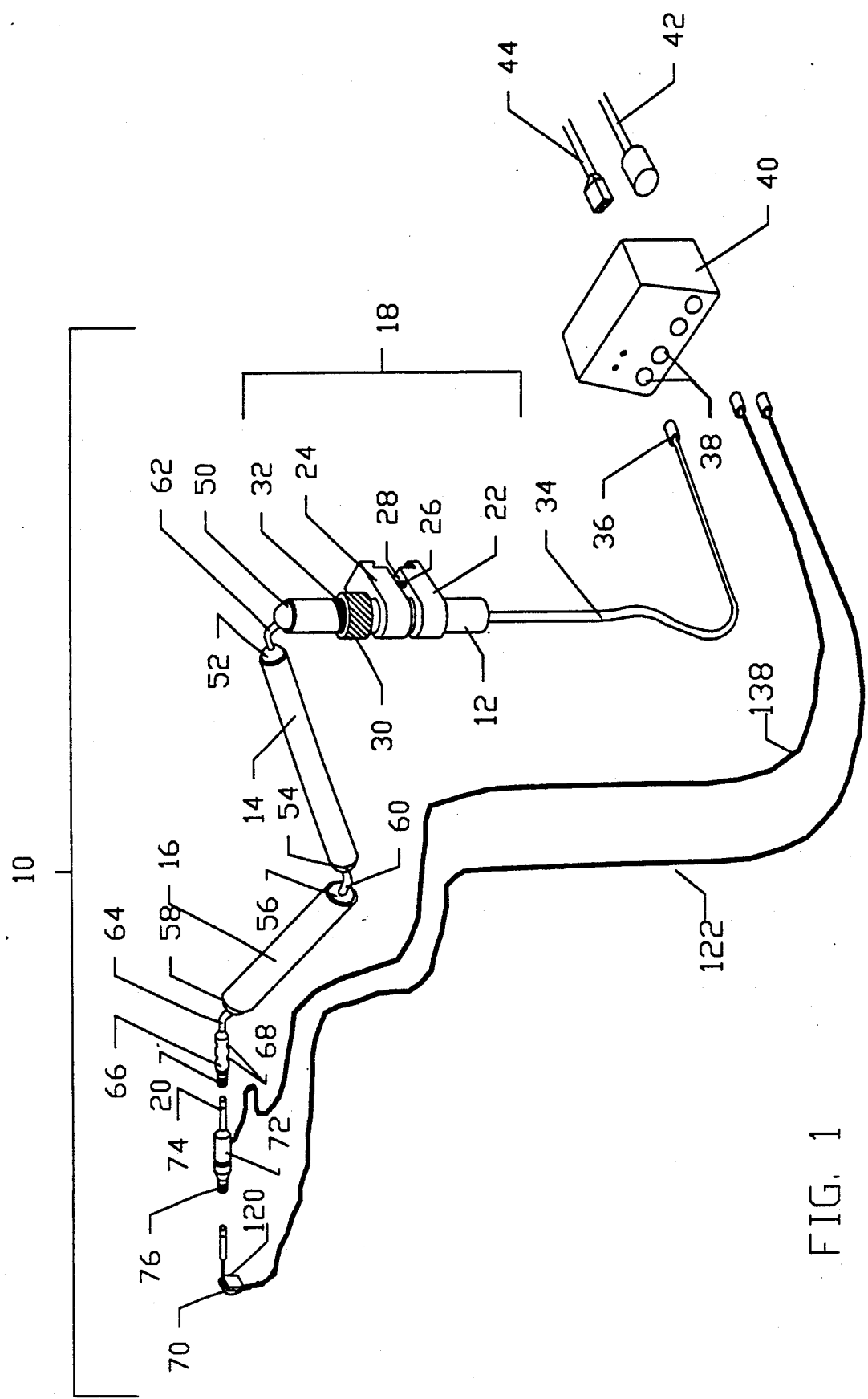
FIG. 1 Is a pictorial illustration of a surgical retractor system for assisting in the performance of surgical procedures.

FIG. 1 is a pictorial illustration of one possible configuration of surgical retractor 10 according to the invention, as it would be used for positioning retractor blades for a typical surgical procedure. In this configuration, surgical retractor 10 constitutes three positioning members, 12, 14, and 16, which are connected together, and in turn are connected to table mounting means 18 and connecting mechanism 20.

Table mounting means 18 is clamped to the side rail of an operating room table, so that surgical retractor 10 will move in the same reference frame as the patient's entire body when the patient's entire body is re-positioned by adjusting the height, tilt or orientation of the operating room table. Table mounting means 18 consists of two jaws, fixed lower jaw 22 attached to proximal positioning member 12 and movable upper jaw 24 which slides on proximal positioning member 12. Spring 26 and rod 28 provide a restoring force and guide, respectively, to keep upper jaw 24 and lower jaw 22 apart to facilitate attachment to the table rail. Knurled knob 30 travels on threaded cover 32, which is fixed to proximal positioning member 12. As knurled knob 30 is rotated, it travels downwards along threaded cover 32, making contact with moveable upper jaw 24, which forces moveable upper jaw 24 down towards fixed lower jaw 22, thereby clamping the operating room table rail between upper jaw 24 and lower jaw 22 to affix surgical retractor 10 rigidly to the operating room table rail.

Exiting the bottom of proximal positioning member 12 is cable 34, which contain air hoses for transporting the pressurized gas that locks the joints of surgical retractor 10, and electrical lines for controlling surgical retractor 10. Cable 34 is terminated with pneumatic-/electrical plug 36 (LEMO USA FGG3B144CNAD12). Pneumatic/electrical plug 36 fits into one of the mating pneumatic/electrical receptacles 38 (LEMO USA EGG3B144CNL) on control box 40. Control box 40 contains pneumatic and electrical circuitry and valves to appropriately control the flow of pressurized gas to surgical retractor 10, in response to control signals generated by switches 68 on surgical retractor 10. Connected to control box 40 are pneumatic hose 42, which supplies pressurized gas, and electrical cord 44 which provides electrical power to the control circuitry within control box 40.

In the preferred embodiment, (shown in FIG. 1) ball joints 50, 52, 54, 56, and 58 are located at one end of proximal positioning member 12, and at both ends of middle positioning member 14 and distal positioning member 16. Ball joints 50 and 52, and ball joints 54 and 56 are connected in pairs with 90 degree bent shafts 62 and 60. The combination of ball joints 50, 52, 54, 56, and 58, and 90 degree bent shafts 60 and 62 provide a wide range of motion and many redundant degrees of freedom that permit surgical retractor 10 to be positioned so that proper retractor blade orientation is possible, while not obstructing the surgeon or surgical site. This geometry also allows surgical retractor 10 to fold up conveniently in a compact form for storage or for sterilization. All ball joints, bent shafts and modules advantageously provide an internal path for pneumatic hoses and electrical lines to keep such hoses and lines bundled and protected.

In the preferred embodiment shown in FIG. 1, ball joint 58 of distal module 16 has a 45 degree bent shaft 64 which has at its end switch barrel 66. Switch barrel 66 contains the set of pushbutton switches 68 which allow the user to send control signals to the control circuitry within control box 40, which in turn controls the flow of pressurized gas to surgical retractor 10. At the end of switch barrel 66 is connecting mechanism 20, to which can be connected either retractor blade 70, or sensing and regulation component 72. At one end of sensing and regulation component 72 is stud 74 that fits into connecting mechanism 20 to attach sensing and regulation component 72 to surgical retractor 10. At the other end of sensing and regulation component 72 is connecting mechanism 76, which is similar to connecting mechanism 20, and to which can be connected retractor blade 70.

Connected to retractor blade 70 is pressure sensor 120, which is connected to signal wire 122, which may be connected to the control circuitry within control box 40. Coming from sensing and regulation component 72 is cable 138, which contains pneumatic and electrical lines for controlling sensing and regulation component 72.

Figure 2:
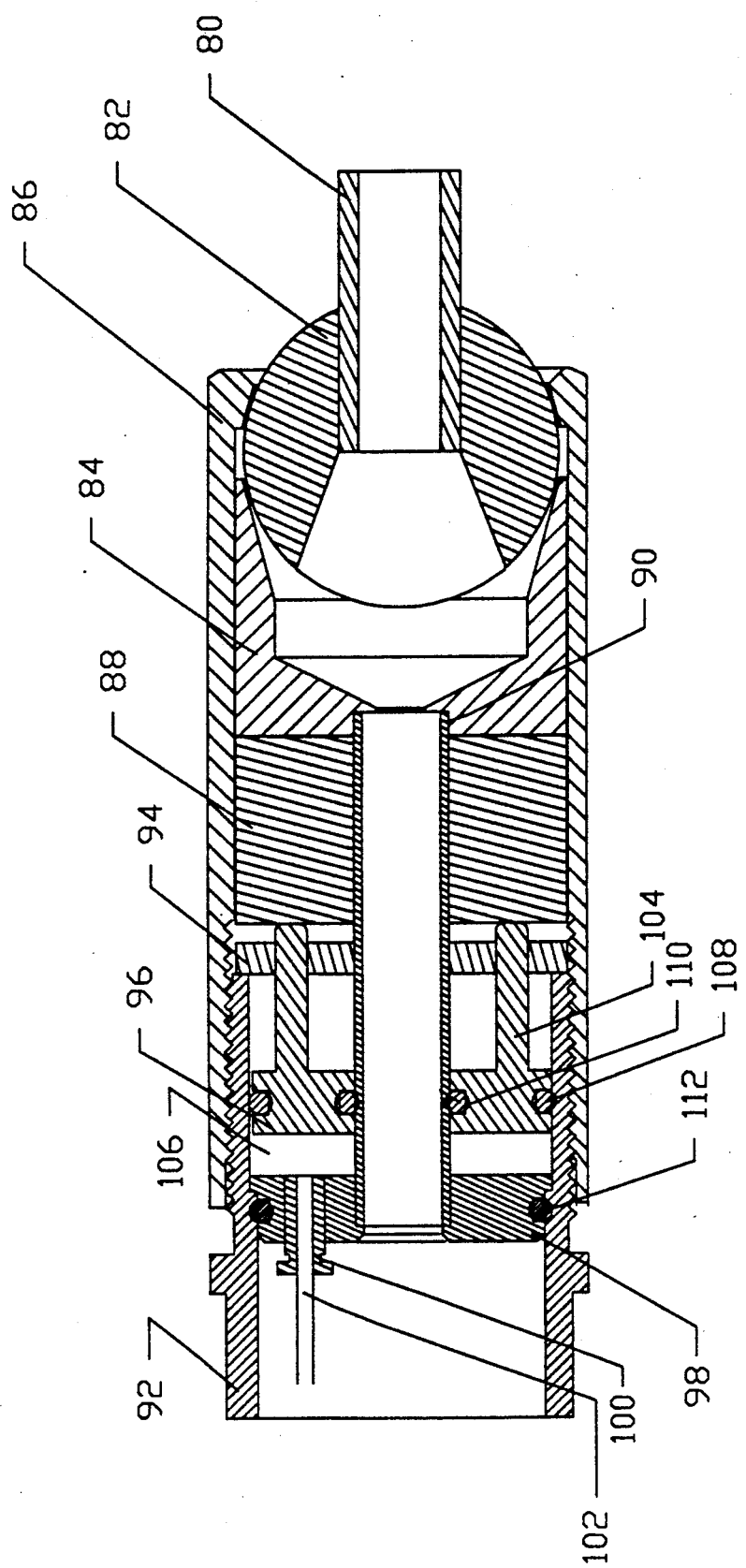
FIG. 2 is a cross section drawing of one joint of the surgical retractor of FIG. 1.

A typical ball joint mechanism as shown in FIG. 2 consists of shaft 80, ball 82, cup 84, threaded cap 86, flexible solid plug 88, routing tube 90, threaded module insert 92, separator plate 94, piston 96, back plate 98, pneumatic hose fitting 100, and pneumatic hose 102. Shaft 80 is a hollow stainless steel shaft which is welded to stainless steel ball 82, which has an internal channel for routing hoses and cables. Ball 82 is sandwiched between aluminum cup 84 and threaded cap 86, both having appropriately contoured surfaces for improving their contact with ball 86, and hard anodized finishes to provide a hard, durable contact surface. Contained between routing tube 90, cap 86, cup 84 and separator plate 94 is flexible solid plug 88, which in the preferred embodiment is constructed of rubber, although any substantially incompressible, flexible, solid material can be used in place of rubber to form the plug. Plunging into flexible solid plug 88 through separator plate 94 are plungers 104 of piston 96. Piston 96 is free to travel along the inner surface of threaded insert 92 and the outer surface of routing tube 90. Between piston 96 and back plate 98 is sealed air space 106, sealed by o-rings 108 and 110 on piston 96 and by o-ring 112 on back plate 98. Back plate 98 is seated within threaded insert 92 and has connected to it pneumatic fitting 100 and routing tube 90. The combination of shaft 80, ball 82, cup 84 routing tube 90, and threaded insert 92 provide a clear path through the ball joint mechanism, through which may be passed electrical wires or pneumatic hoses.

In use, the ball joint mechanism can be activated with pressurized gas to lock the ball joint in place. In the relaxed state, threaded cap 86 is threaded onto threaded insert 92 to fit cap 86, ball 82, cup 84, flexible solid plug 88, piston 96, and back plate 98 together in close contact prior to pressurization. When activated, pneumatic supply hose 102 supplies pressurized gas to sealed air space 106. The pressurized gas in sealed air space 106 pushes against piston 96 and causes it to move so as to force plungers 104 through separator plate 94 and into flexible solid plug 88. Flexible solid plug 88 then becomes pressurized because it is constrained on all sides by separator plate 94, routing tube 90, cup 84, and cap 86, hence cannot be substantially displaced when plungers 104 are driven into it. In this way, flexible solid plug 88 behaves like an incompressible hydraulic fluid. Pressurized flexible solid plug 88 then exerts pressure against cup 84 to create a high force which compresses ball 82 between cup 84 and cap 86, thereby increasing the friction force between ball 82, cup 84 and cap 86, which locks ball 82 in position. The activating force applied to piston 96 by the pressurized gas is proportional to the pressure of the pressurized gas supply multiplied by the area of piston 96. This force is transmitted by plungers 104 to flexible plug 88. The pressure applied to flexible plug 88 is proportional to the force applied by plungers 104, divided by the total cross sectional area of plungers 104. In the preferred embodiment, the total cross sectional area of plungers 104 is chosen to be smaller than the area of piston 96, hence the pressure in flexible plug 88 is higher than the pressure of the pressurized gas supply in sealed air space 106. The pressure in flexible plug 88 is applied over the back surface of cup 84, the area of which is much larger than the total cross sectional area of plungers 104. As the force applied to cup 84 is proportional to the pressure applied to the back of cup 84 multiplied by the area of contact between the back of cup 84 and flexible plug 88, a large force is applied to cup 84, resulting in high locking forces being applied to ball 82.

Surgical retractor 10 can be used as a simple positioner with no sensing and regulating capabilities by attaching retractor blade 70 directly into connecting mechanism 20. If tissue pressure sensing and regulating functions are desired, sensing and regulation component 72 is connected to connecting mechanism 20 and retractor blade 70 is connected to connecting mechanism 76 of sensing and regulating component 72.

Figure 3:
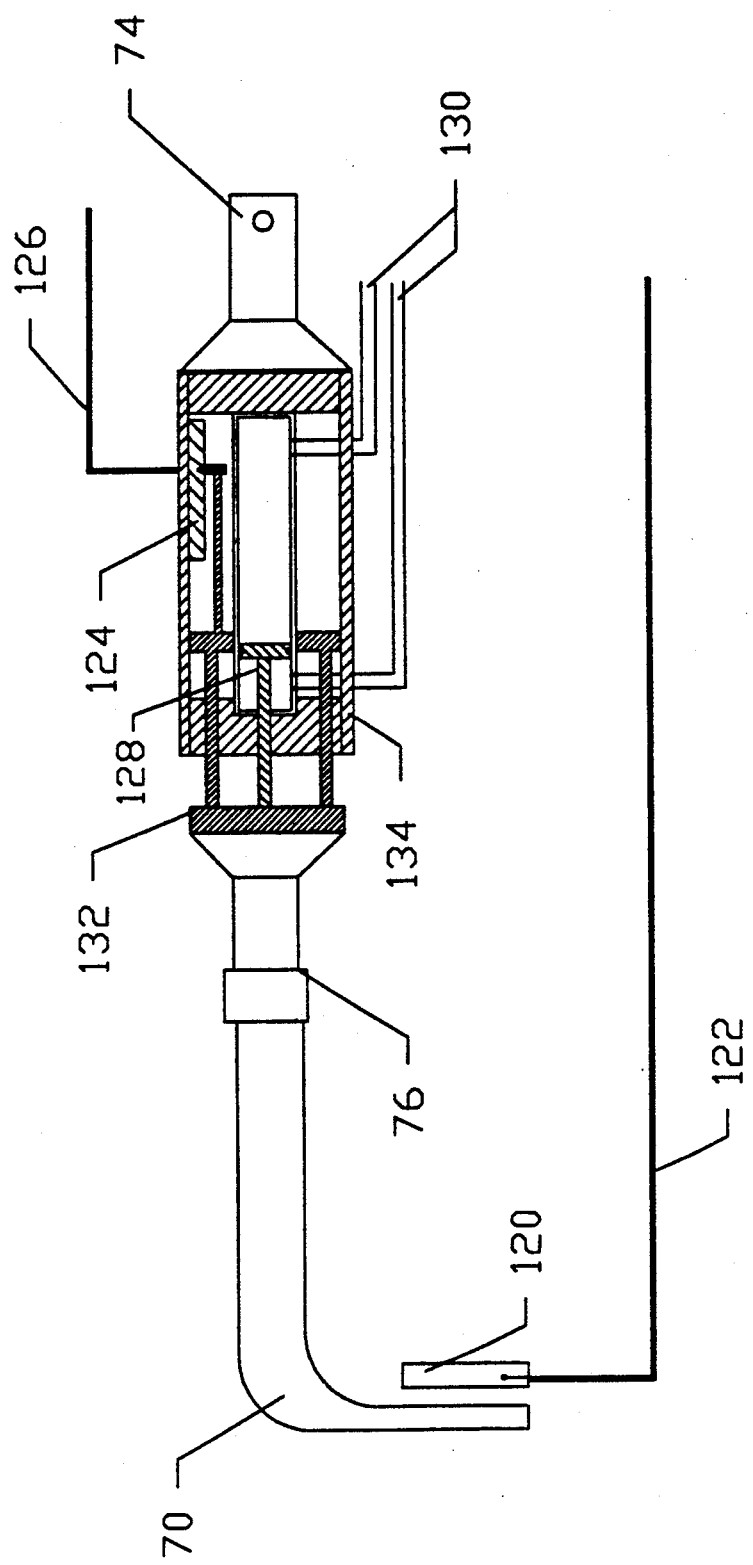
FIG. 3 is a simplified cross section drawing of the retractor blade pressure sensing and position regulating component of the surgical retractor system of FIG. 1.

Sensing and regulating component 72 is shown in FIG. 3. Pressure sensor 120 is attached to the contact surface of surgical retractor blade 70, and is connected to pressure information signal wire 122, which in turn is connected to control circuitry located in control box 40. Movement of retractor blade 70 is accomplished by changing the position of moving component 132 with respect to fixed component 134. Located within fixed component 134 is position sensor 124, which in the preferred embodiment is a linear potentiometer which is connected between fixed component 134 and moving component 132, so that the relative position of moving component 132 with respect to fixed component 134 can be measured. Also located within and attached to fixed component 134 is double acting piston 128. The push rod of double acting piston 128 is connected to moving component 132, so that double acting piston 128 can either push apart or pull together fixed component 134 and moving component 132. Double acting piston 128 is connected to pressurized gas supply lines 130, which in turn are connected to control box 40. Pressurized gas supply lines 130 supply pressurized gas to double acting piston 128 in order to either push apart or pull together fixed component 134 and moving component 132, which has the effect of altering the position of retractor blade 70 with respect to attachment stud 74, and hence with respect to surgical retractor 10.

Figure 4:
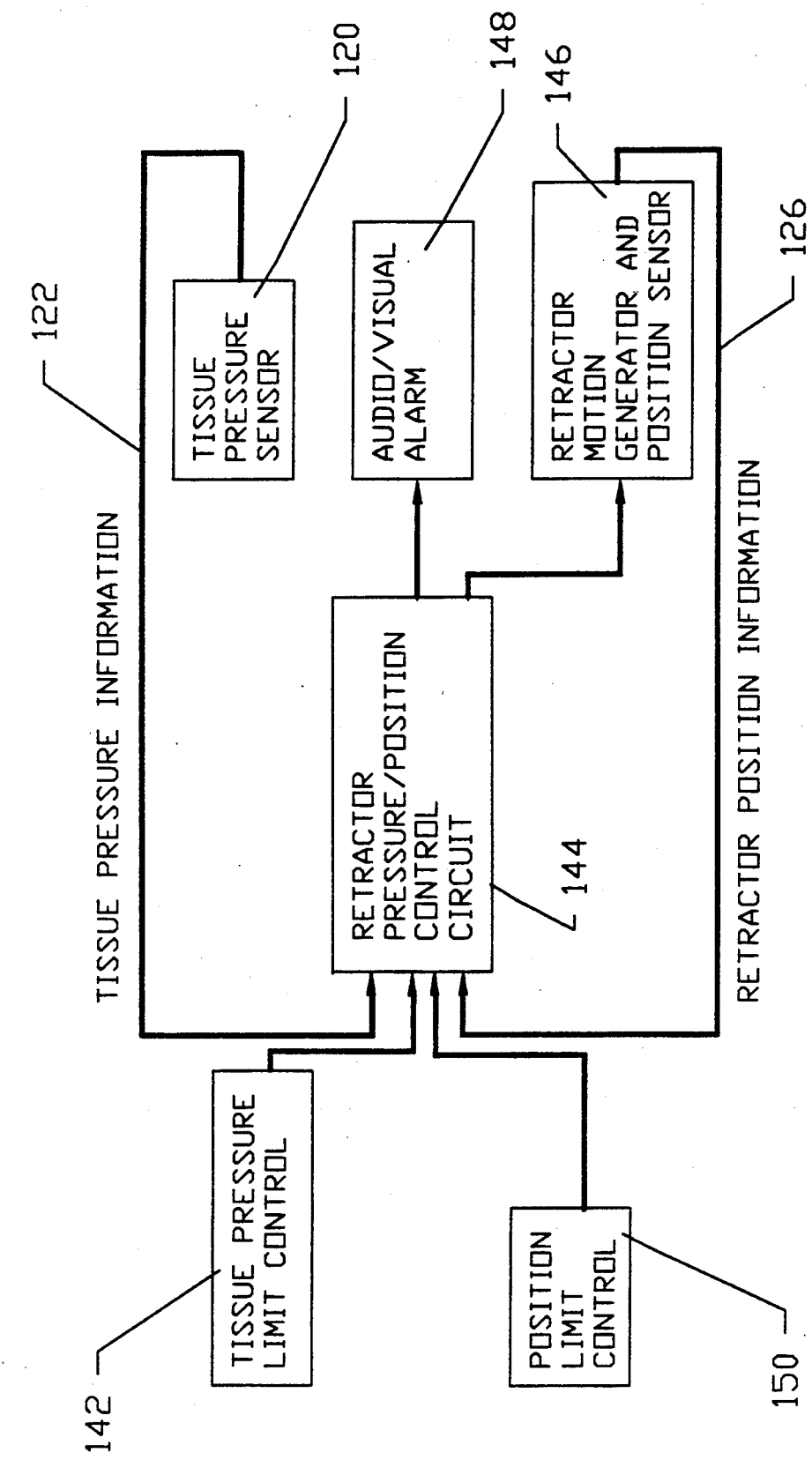
FIG. 4 is a block diagram of the control system for the pressure sensing and position regulating component of FIG. 3.

FIG. 4 shows a simplified block diagram of the control system for controlling the operation of sensing and regulating component 72. In operation, the user may choose to adjust either the range of tissue pressures or the range of positions allowable, using tissue pressure limit control 142 or position limit control 150. If no adjustment is desired, automatically selected default values for these parameters will be used by pressure/position control circuit 144. Pressure/position control circuit 144 operates by comparing tissue pressure information sensed by tissue pressure sensor 120 with the tissue pressure limits set by the user or by default. If the tissue pressure sensed is outside the set limits, pressure/position control circuit 144 sends a signal to retractor motion generator and position sensor 146 to cause it to move retractor blade 70 in a direction which will either increase or decrease the tissue pressure as appropriate. Retractor position information from retractor motion generator and position sensor 146 is then compared with the position limits set by the user or by default. If pressure/position control circuit 144 is unable to keep retractor blade 70 in a position which is within the range of allowable positions set by the user or by default, or is unable to keep retractor blade 70 in a position which keeps the tissue pressure sensed by tissue pressure sensor 120 within the range of allowable tissue pressures set by the user or by default, audio/visual alarm 148 is activated to warn the user.

OPERATION BY SURGICAL STAFF

Before using surgical retractor 10 in a surgical procedure, a user must choose and sterilize appropriate retractor blades, and sterilize surgical retractor 10. The preferred method for sterilizing retractor position 10 is to steam sterilize (autoclave) the retraction system, a relatively rapid technique (30 minutes) commonly used in hospitals, utilizing high temperatures to sterilize medical instrumentation. Other sterilization methods may be used if desired, including chemical sterilization with ethylene oxide, a slow procedure lasting typically 18 hours; or draping surgical retractor 10 with a sterile cover.

The patient is first positioned on the operating room table in a normal position for the surgical procedure to be performed, and anesthetized in accordance with standard medical procedures.

Sterilized surgical retractor 10 is attached to a suitable place on the operating room table by first loosening knurled knob 30 (shown in FIG. 1), which allows spring 28 to force apart fixed jaw 22 and sliding jaw 24 of proximal positioning member 12. This allows the operating room table accessory rail to be inserted between jaws 22 and 24. Knurled knob 30 is then tightened to force sliding jaw 24 towards fixed jaw 22, thereby clamping the operating room table rail between jaws 22 and 24 to rigidly fix surgical retractor 10 to the operating room table.

Pneumatic/electrical plug 36 of sterilized surgical retractor 10 is attached to pneumatic/electrical receptacle 38 of control box 40, which may be located away from the operating room table. Electrical power plug 44 and pressurized gas supply hose 42 are connected to control box 40 to provide appropriate electrical and pneumatic power for surgical retractor 10.

If the operating surgeon wishes to use sensing and regulating component 72, it should be connected to connecting means 20, after which tissue pressure signal wires 122 and cable 138 should be connected to control box 40.

The operating surgeon should then select an appropriate retractor blade 70 and connect it to surgical retractor 10 or sensing and regulating component 72. Retractor blade 70 may be changed at any time during the procedure for a different retractor blade by removing the old retractor blade from connecting means 20 on surgical retractor 10 or connecting means 76 on sensing and regulating component 72, and replacing it with an new one.

Before using sensing and regulating component 72 in the surgical procedure, the operating surgeon should select and set tissue pressure and position limits appropriate for the surgical procedure to be performed.

In using surgical retractor 10, the operating surgeon may desire to change the position of retractor blade 70 or surgical retractor 10. If the desired change in position is small, operating surgeon may choose to move only part of positioning modules 12, 14, or 16 of surgical retractor 10. To do this, the operating surgeon presses one of the pushbutton 68 on switch barrel 66, which sends a control signal to control box 40. This control signal activates the appropriate valve in the pneumatic circuit in control box 40 that provides pressurized gas to the locking mechanisms of the particular ball joints that the operating surgeon has chosen to unlock. With the valve activated, the locking mechanisms of the chosen ball joints are no longer pressurized and the ball joints are released to move freely. The operating surgeon may now re-position retractor blade 70 and the chosen unlocked ball joints. When a new desired position is reached, the operating surgeon releases the pushbutton 68, which de-activates the appropriate valve, causing the locking mechanisms to be re-pressurized, thereby locking surgical retractor 10 in the new desired orientation.

If the desired change in position is large, the operating surgeon may choose to move all positioning modules 12, 14, and 16 of surgical retractor 10. To do this, the operating surgeon presses a different pushbutton 68 on switch barrel 66, which sends a control signal to control box 40. This control signal activates all valves in the pneumatic circuit in control box 40 that service all the locking mechanisms of surgical retractor 10. With all valves activated, all the locking mechanisms are no longer pressurized and all balls joints are released to move freely. The operating surgeon may now re-position retractor blade 70 and all modules of surgical retractor 10. When a new desired position is reached, the operating surgeon releases pushbutton 68, which deactivates the valves, causing all the locking mechanisms to be re-pressurized, thereby locking surgical retractor 10 in the new desired orientation.

In using surgical retractor 10, the operating surgeon may wish to alter the sensing and regulation functions of sensing and regulating component 72. At any time during the procedure, the surgeon may change the position or tissue pressure limit settings, that if exceeded will activate an alarm to alert the surgeon that an unacceptable tissue pressure or position has been detected.

When the surgical procedure is complete, retractor blade 70 is removed from surgical retractor 10, electrical/pneumatic plug 36 is removed from electrical/pneumatic receptacle 38 of control box 40, and knurled knob 30 is loosened to allow jaws 22 and 24 to separate and release their grip on the operating room table rail. Electrical plug 44 and pneumatic hose 42 are then disconnected from control box 40, and surgical retractor 10 and control box 40 are then removed to storage.

Many alterations and adaptations may be made to the preferred embodiment described herein. Accordingly, the invention is to be limited only by reference to appended claims. For example, although the preferred embodiment herein described consists of three positioning members, more or fewer positioning members could be used for increased functional capability. The size of these members can also be changed to better suit the requirements of the surgical procedure in which the invention is being used. The tissue pressure sensor used with the sensing and regulating component could be replaced with multiple pressure sensors, or other types of sensors for measuring other physiological or morphological parameters, including, for example, temperature, color, or pH. Also, the double acting pneumatic cylinder used in sensing and regulating component 72 could be replaced with other pneumatic, hydraulic, or electric actuators to achieve a similar function. Likewise, the locking mechanism used with the ball joints of the preferred embodiment can utilize means to force plungers 104 into flexible solid plug 88 other than air pressure, and can employ materials other than rubber in place of flexible solid plug 88. Flexible solid plugs of various geometries, or of a number of separate pieces, where the pieces could be of varying hardness, or of a number of lubricated layers arranged so as to slide upon one another, or plugs of deformable, non-flexible materials could be used to improve the performance of the force multiplier. A similar force amplification means could be used with selectably positionable joints of geometries other than that of the ball and socket type used in the preferred embodiment. Furthermore, the positioning apparatus could also be equipped with a variety of retractors or instrument holders to grip other surgical instrumentation, such as arthroscopy cameras, suction catheters, light sources, and other tools or apparatus which must be positioned near the surgical site; pushbutton 68 herein described in the preferred embodiment could be replaced with a number of different switching mechanisms, including footswitches, voice control devices, or remote control pendants; and the tissue pressure sensing and regulating component described in the preferred embodiment could be utilized with many other retractor supporting means.

We claim:

1. An apparatus for amplifying and applying a force, comprising:
    a container;
    a nonhomogeneous, deformable member disposed within the container, the deformable member having a first side and a second side;
    a part disposed within the container and having a face adjacent to the second side of the deformable member;
    force means for applying a force to a first surface area located on the first side of the deformable member, the area of the face of the part being larger than the first surface area of the deformable member, the container, deformable member, and part being arranged so that the force applied to the first surface area is applied to the area of the part face.

2. The apparatus of claim 1 wherein the deformable member comprises a plurality of portions of varying hardness.

3. The apparatus of claim 1 wherein the hardness of the deformable member varies between the first and second sides.

4. The apparatus of claim 1 wherein the deformable member is constructed of a plurality of pieces that are movable relative to one another.

5. A joint apparatus, comprising:
    a tubular member;
    a sphere retained within one end of the tubular member;
    a cup member, contained within the tubular member and slidable therein into a locking position for preventing rotation of the sphere relative to the tubular member;
    a piston slidably contained within the tubular member and having a first surface and opposing second surface, the second surface having an area substantially less than the area of the first surface;
    a substantially incompressible, flexible plug member contained within the tubular member between the second surface of the piston and a face of the cup member; and
    force means for applying a force to the first surface of the piston, the tubular member, cup member, piston, and plug member being arranged so that the force applied to the first surface of the piston is applied by the plug member to the face of the cup member for moving the cup member into the locking position.

6. The apparatus of claim 5 wherein the force means includes a plate sealed within the tubular member for defining a pressurizable space near the first surface of the piston.

7. The apparatus of claim 6 further comprising a second tubular member connected between the cup member and the plate for defining a discrete passageway that extends through the pressurizable space.

8. The apparatus of claim 7 wherein the sphere includes an opening for defining in combination with the passageway a continuous path through the joint apparatus.

* * * * *